(12) United States Patent  
Bicer

(10) Patent No.: US 7,842,084 B2  
(45) Date of Patent: Nov. 30, 2010

(54) METHOD AND SYSTEMS FOR SIZING, FOLDING, HOLDING, AND DELIVERING A HEART VALVE PROSTHESIS

(75) Inventor: Demetrio Bicer, Trabuco Canyon, CA (US)

(73) Assignee: 3F Therapeutics, Inc.

( * ) Notice: Subject to any disclaimer, the term of this patent is extended or adjusted under 35 U.S.C. 154(b) by 1197 days.

(21) Appl. No.: 11/471,092

(22) Filed: Jun. 19, 2006

(65) Prior Publication Data

US 2006/0287718 A1 Dec. 21, 2006

Related U.S. Application Data

(60) Provisional application No. 60/761,532, filed on Jan. 23, 2006, provisional application No. 60/700,354, filed on Jul. 19, 2005, provisional application No. 60/692,274, filed on Jun. 21, 2005.

(51) Int. Cl.
*A61F 2/24* (2006.01)
*A61F 2/06* (2006.01)
*A61F 11/00* (2006.01)

(52) U.S. Cl. .................. 623/2.11; 623/1.11; 623/1.23; 606/108

(58) Field of Classification Search ............... 623/2.11, 623/1.11, 1.12, 1.23, 2.14, 2.17, 2.18; 606/108, 606/139
See application file for complete search history.

(56) References Cited

U.S. PATENT DOCUMENTS

| | | | |
|---|---|---|---|
| 4,451,936 A | | 6/1984 | Carpentier et al. |
| 4,679,556 A | * | 7/1987 | Lubock et al. .............. 606/1 |
| 5,236,450 A | * | 8/1993 | Scott .......................... 623/2.11 |
| 5,443,502 A | * | 8/1995 | Caudillo et al. ............. 623/2.11 |
| 5,476,510 A | * | 12/1995 | Eberhardt et al. ........... 623/2.11 |
| 5,578,076 A | * | 11/1996 | Krueger et al. ............. 623/2.11 |
| 5,833,694 A | * | 11/1998 | Poncet ....................... 623/1.11 |
| 6,017,362 A | * | 1/2000 | Lau ............................. 623/1.2 |
| 6,197,053 B1 | * | 3/2001 | Cosgrove et al. ........... 623/2.11 |
| 6,416,547 B1 | * | 7/2002 | Erickson et al. ............ 623/2.11 |
| 6,736,845 B2 | | 5/2004 | Marquez et al. |
| 7,101,396 B2 | | 9/2006 | Artof et al. |
| 2002/0013621 A1 | | 1/2002 | Stobie et al. |
| 2002/0133226 A1 | * | 9/2002 | Marquez et al. ............. 623/2.11 |
| 2003/0130729 A1 | | 7/2003 | Paniagua et al. |
| 2004/0059412 A1 | * | 3/2004 | Lytle, IV et al. ........... 623/2.11 |
| 2005/0075731 A1 | | 4/2005 | Artof et al. |
| 2005/0182486 A1 | * | 8/2005 | Gabbay ..................... 623/2.11 |
| 2005/0203615 A1 | | 9/2005 | Forster et al. |
| 2006/0161249 A1 | * | 7/2006 | Realyvasquez et al. .... 623/2.11 |
| 2006/0271081 A1 | * | 11/2006 | Realyvasquez ............. 606/170 |
| 2007/0255093 A1 | * | 11/2007 | Lau et al. ..................... 600/37 |

FOREIGN PATENT DOCUMENTS

WO WO-2005-084595 9/2005

\* cited by examiner

*Primary Examiner*—(Jackie) Tan-Uyen T Ho  
*Assistant Examiner*—Jing Rui Ou  
(74) *Attorney, Agent, or Firm*—Mike Jaro; Jeffrey J. Hohenshell

(57) ABSTRACT

A folding device used to fold a cardiac valve is disclosed. Also shown are methods and system for holding and delivering a cardiac valve during implantation. The folding device facilitates folding either a stented or unstented prosthetic valve prior to insertion into a valve annulus. A delivery system is provided to allow a user to measure the patient annulus to select the prosthetic valve size and insert a folded prosthetic valve into a target site. Methods for using the folding device and delivery system are also disclosed.

4 Claims, 25 Drawing Sheets ced Jan. 23, 2006 all of which are incorporated herein by reference

METHOD AND SYSTEMS FOR SIZING, FOLDING, HOLDING, AND DELIVERING A HEART VALVE PROSTHESIS

REFERENCE TO RELATED APPLICATIONS

This application claims priority to Provisional Application Ser. No. 60/692,274 filed Jun. 21, 2005; and Provisional Application Ser. No. 60/700,354 filed Jul. 19, 2005; and Provisional Application Ser. No. 60/761,532 filed Jan. 23, 2006 all of which are incorporated herein by reference

FIELD OF APPLICATION

The present invention relates to methods and systems for sizing, folding, holding, transferring and delivering a heart valve prosthesis during implantation. In particular, the present invention relates to biological tissue heart valves manufactured from a flexible material or a shape memory alloy.

BACKGROUND OF THE INVENTION

Heart valve replacement is required when a patient's heart valve becomes diseased or damaged. Surgically implanted heart valve prostheses have extended the life expectancy of many patients with defective heart valves. Such prostheses can be either mechanical or biological (tissue valves), stented an/or stentless and may be implanted into the aortic, mitral, tricuspid, or pulmonary position.

During this surgical procedure, the heart is typically stopped, and the patient attached to a heart/lung bypass machine that pumps and oxygenates the patient's blood. The longer a patient is required to rely on the artificial heart/lung bypass machine to maintain vital functions, the greater the stress on the patient. There is consequently a need to simplify the surgical implantation of a heart valve prosthesis into the implantation annulus in order to minimize both the length of surgery and the amount of time spent on heart/lung bypass.

New stented biological valves made from flexible material or from materials that exhibit shape memory characteristics promise less complicated and faster valve implant procedures. Such valves may be folded to reduce their size for delivery to a target site, and re-expanded when in position. Such valves are sometimes referred to as suture-less valves since they may be implanted and secured into the patient's annulus without the use of sutures. In some instances, one, two, three, or a plurality of sutures are utilized to guide the valves into position. An example of such a valve is Artof et al., Minimally Invasive Valve Replacement System, U.S. patent application Ser. No. 10/680,071, issued as U.S. Pat. No. 7,101,396 on Sep. 5, 2006, hereby incorporated by reference.

The limited view of and access to an implantation site makes insertion of bioprosthetic valves difficult and time consuming. The valve itself may also reduce the surgeon's view of the implantation site, making valve positioning difficult. In the case of surgical aortic valve replacements, a small slit is sometimes made through the patient's aorta so that the malfunctioning valve can be removed and replaced with a prosthetic valve. Both disposable and non-disposable valve holders are used to help position the valve during surgery. Known valve holders, however, are large and cumbersome and obstruct the surgeon's view. Current valve holders are also not adapted to receive valves that exhibit shape memory characteristics. Therefore, what are needed are methods and systems for performing valve surgery as quickly as possible to ensure consistent and accurate placement of the prosthesis.

SUMMARY OF THE INVENTION

The present invention provides methods and systems for sizing, folding, holding, transferring, and delivering a heart valve prosthesis during implantation. A suitable heart valve prosthesis is that of Artof et al., Minimally Invasive Valve Replacement System, U.S. patent application Ser. No. 10/680,071. Such a valve may be folded, delivered to the target site, and re-expanded when into position. It is important that the valve is accurately and consistently folded and delivered to its target site. Accordingly, it is one object of the present invention to provide systems and methods for reducing the complexity of sizing, holding, and delivering a foldable valve to its target site in or near a heart. It is another object of the present invention to provide systems and methods to ensure faster and more accurate delivery of a foldable valve to its target site in or near a heart.

In one embodiment of the present invention, the target site is the aortic valve annulus. In another embodiment of the present invention, the target site is the mitral valve annulus. In another embodiment of the present invention, the target site is the tricuspid valve annulus. In yet another embodiment of the present invention, the target site is the pulmonary valve annulus.

In one embodiment of the present invention, a folding device is disclosed that assists with the folding of the valve.

In another embodiment of the present invention, a valve delivery system is provided that includes a valve receptacle adapted to receive a handle. The valve delivery system can help the surgeon with valve sizing by providing a full set of different sizes of external diameter to select the right size by measuring the patient annulus of implant. Primarily, the valve delivery system assists the surgeon with heart valve delivery. The folded cardiac valve is loosely disposed within the valve receptacle. The cardiac valve is released by pulling the delivery system away from the target site, leaving the cardiac valve in position.

In another embodiment of the present invention, a valve delivery system is disclosed that includes a folding device adapted to receive a handle. The folded cardiac valve is loosely disposed within the valve receptacle. The cardiac valve is released by pulling the delivery system away from the target site, leaving the cardiac valve in place.

In yet another embodiment of the present invention, a valve delivery system is provided that includes a retainer ring adapted to receive a handle. The folded cardiac valve is loosely disposed within the retainer ring. The cardiac valve is transferred to the implantation site. The cardiac valve is then released by pulling the delivery system away from the implantation site, leaving the cardiac valve disposed within the implantation annulus.

The above aspects and other objects, features and advantages of the present invention will become apparent to those skilled in the art from the following description of the preferred embodiments taken together with the accompanying figures.

DESCRIPTION OF THE PREFERRED EMBODIMENTS

FIGS. 1 through 23 show embodiments of systems and methods for folding and delivering a cardiac valve.

Folding Device

Figure 1:
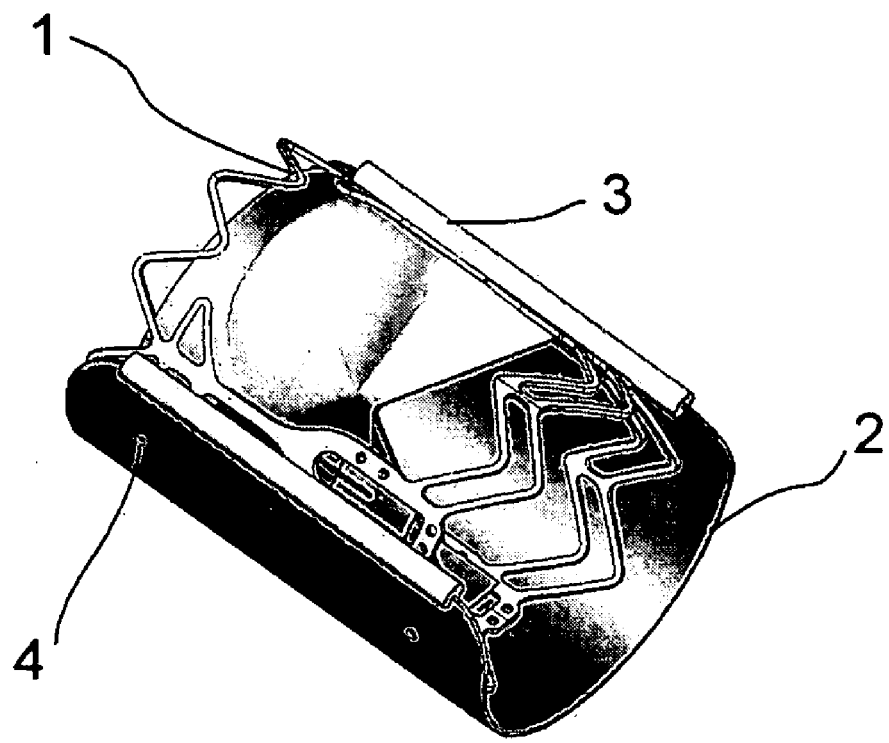
FIG. 1 shows a perspective view of an expanded heart valve loosely disposed within in the folding device.
Figure 2:
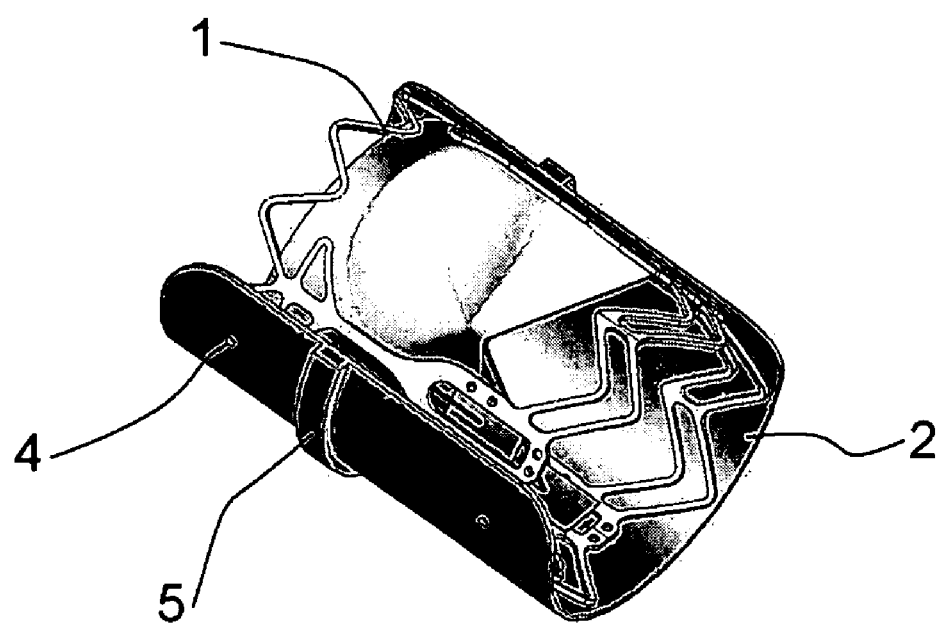
FIG. 2 shows a perspective view of an expanded heart valve loosely disposed within the folding device.

As shown in FIG. 1 and FIG. 2, the present invention is directed towards a folding device 2. The folding device 2 may be securely attached to an unfolded prosthetic valve 1. A surgeon or an assistant folds the unfolded valve 1 by pushing the exposed side walls of the prosthetic valve 1 towards the center of the folding device 2 while simultaneously using fingers to compress the sides of the folding device 2. The folding device 2 bend inwards and the prosthetic valve 1 folds by caving in on itself.

The valve 1 may be inserted into the folding device 2 in the operating room. Alternatively, the valve 1 may be inserted and attached into the folding device 2 during the manufacturing process. As such, the folding device 2 also protects the valve 1 during shipment. The folding device 2 helps make sure foldable valves are folded consistently. The folding device 2 also helps transfer the prosthetic valve 1 in a folded configuration to the target valve annulus. The folding device 2 may also be used as a stand-alone device to fold and deliver a prosthetic valve 1. The folding device 2 may also be used in conjunction with a valve delivery system to deliver a folded valve 1 to a target site.

FIG. 1 and FIG. 2 show the cardiac valve 1 loosely disposed within the folding device 2. The folding device 2 is generally semi-cylindrical, to partially envelope the cardiac valve 1. In one embodiment of the present invention, locking bars 3 are attached to the folding device 2. The locking bars 3 are generally long slender rods used to lock the folding device 2 into a top loading valve receptacle 17 shown in FIG. 18. In another embodiment of the present invention, the locking bars 3 are hollow cylinders that can be loosely disposed on the two rods 22 part of the guide rail valve receptacle 15 shown in FIG. 16A and FIG. 16B. In yet another embodiment, the folding device has curved edges and snaps onto the two rods 22 part of the guide rail valve receptacle 15 shown in FIG. 16A and FIG. 16B.

Sutures 9 may be tied between a plurality of suture holes 4 on opposite sides of the folding device 2 to retain the valve 1 positioned within the folding device 2. Such sutures 9 help retain the position of the prosthetic valve 1 within the folding device 2. As such, the sutures 9 also help with consistent folding of the prosthetic valve 1.

FIG. 2 shows an embodiment of the present invention wherein the folding device has a stopper ring 5 is attached to the folding device 2. The stopper ring 5 is used to guide and limit the insertion of the folding device 2 into a valve receptacle 10.

Figure 3A:
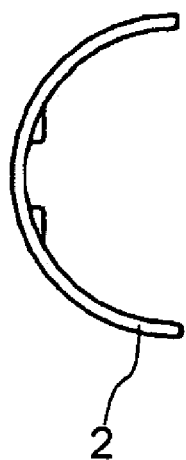
FIGS. 3A and 3B show end and top views, respectively, of the folding device
Figure 3B:
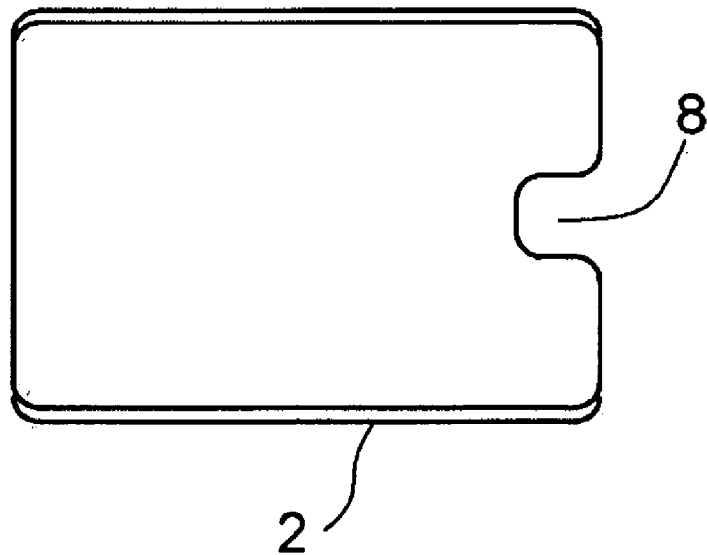

FIGS. 3A and 3B show end and top views, respectively, of the folding device 2. The folding device 2 is generally curved to match the substantially circular geometry of the cardiac valve 1. The folding device may include a single or plurality of suture slots 8. Suture slots 8 may be used to tie guiding sutures between the unfolded prosthetic valve 1 and the valve annulus, or alternatively between the folded prosthetic valve 6 and the valve annulus. In a preferred embodiment of the present invention, the folding device 2 is made out of a flexible material such that the folding device can stay in intimate contact with the cardiac valve 1 during folding. In one embodiment of the present invention, the folding device 2 is made out of a plastic material. In another embodiment of the present invention, the folding device 2 is made out of a metal. In yet another embodiment of the present invention, the folding device 2 is made out of a composite material. The folding device can be cleaned, sterilized in an autoclave, and reused. In another embodiment, the folding device 2 is disposable.

Figure 4A:
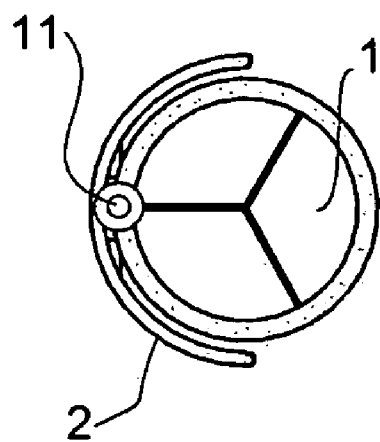
FIGS. 4A and 4B show end and top views, respectively, of an expanded heart valve loosely disposed in the folding device.
Figure 4B:
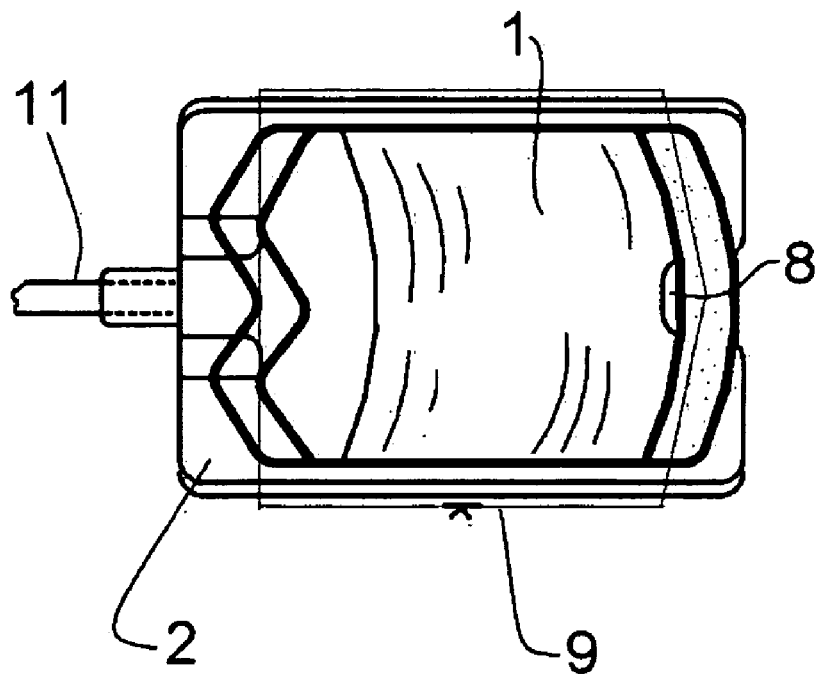

FIGS. 4A and 4B show end and top views, respectively, of an expanded heart valve 1 loosely disposed in the folding device 2. Temporary sutures 9 are tied between suture holes 4 to secure the valve 1 within the folding device 2. FIG. 4B also shows a handle 11 attached directly to the folding device 2. In one embodiment of the present invention, there is no handle 11 attached directly to the folding device 2.

Figure 5A:
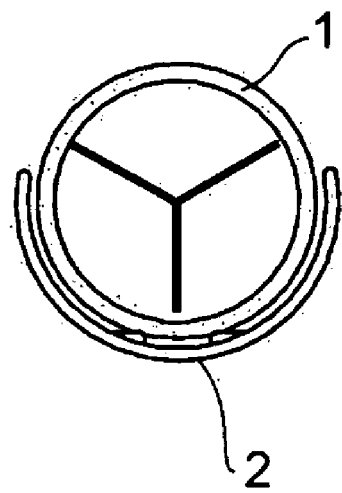
FIGS. 5A and 5B show end and side views, respectively, of an expanded heart valve loosely disposed in the folding device.
Figure 5B:
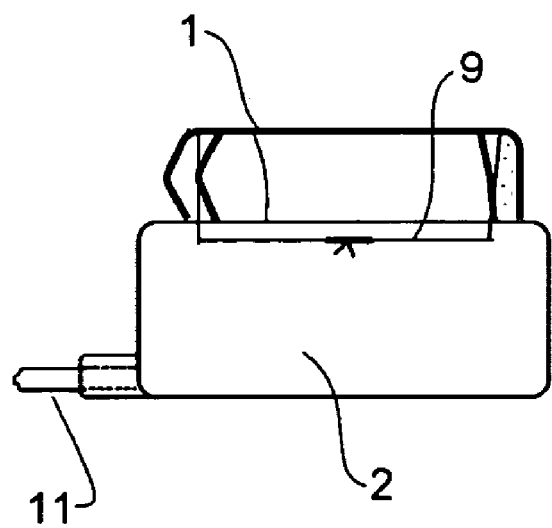

FIGS. 5A and 5B show end and side views, respectively, of an expanded heart valve 1 loosely disposed in the folding device 2.

Figure 6A:
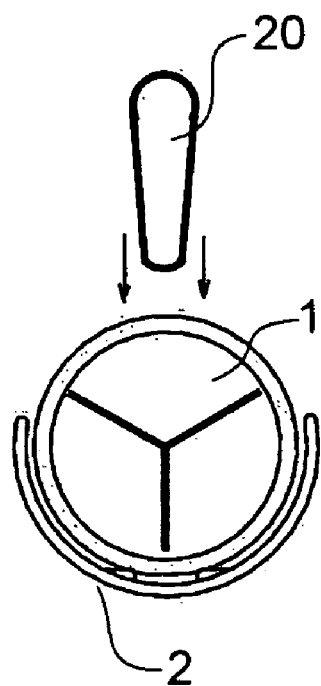
FIGS. 6A and 6B show end and side views, respectively, of a heart valve being folded within the folding device
Figure 6B:
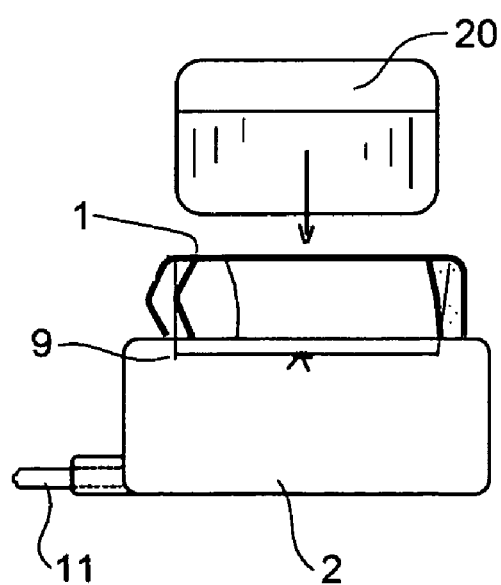

FIGS. 6A and 6B show end and side views, respectively, of a heart valve 1 being folded within the folding device 2. A folding bar 20 used to push the exposed portion of the valve 1 downward into the folding device 2, thereby transforming the unfolded valve 1 into a folded valve 6. The folding bar 20 is used with the folding device 2 to ensure consistent folding of the valve.

Figure 7A:
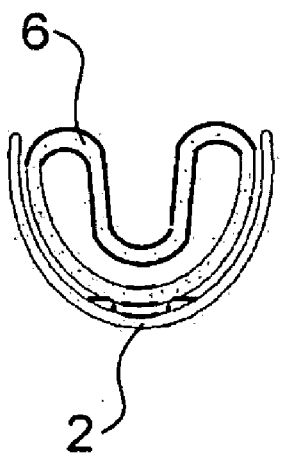
FIGS. 7A and 7B show end and top views, respectively, of a folded heart valve loosely disposed in the folding device.
Figure 7B:
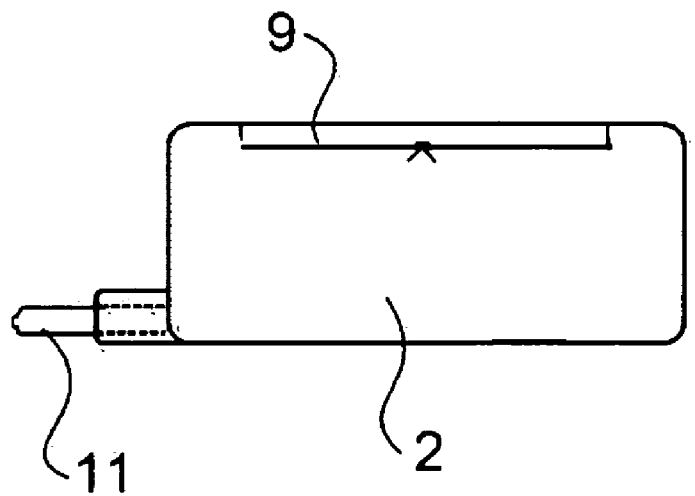
Figure 8:
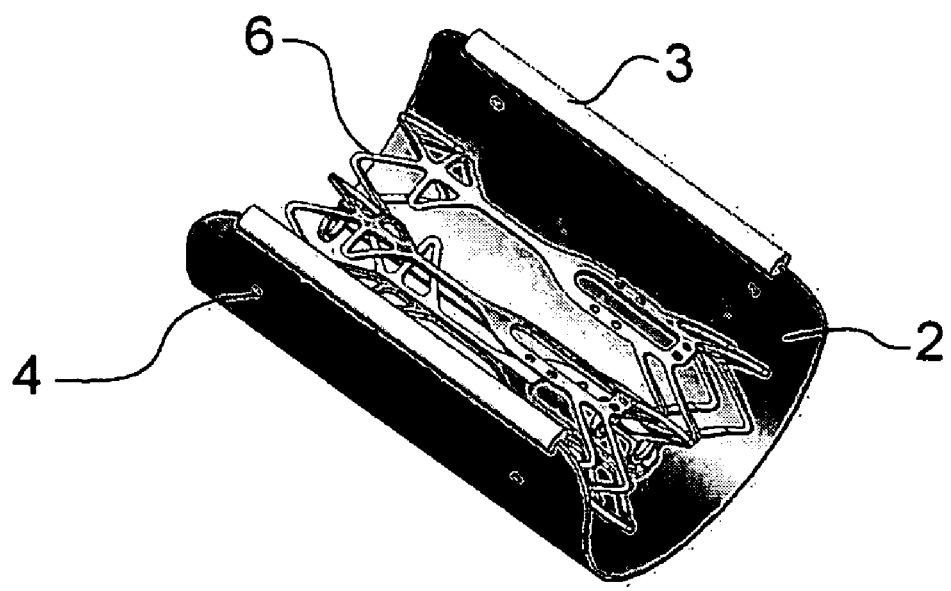
FIG. 8 shows a folded heart valve loosely disposed in the folding device. Parts of the heart valve, including the tissue and cloth cuffs, have been removed for clarity.
Figure 9:
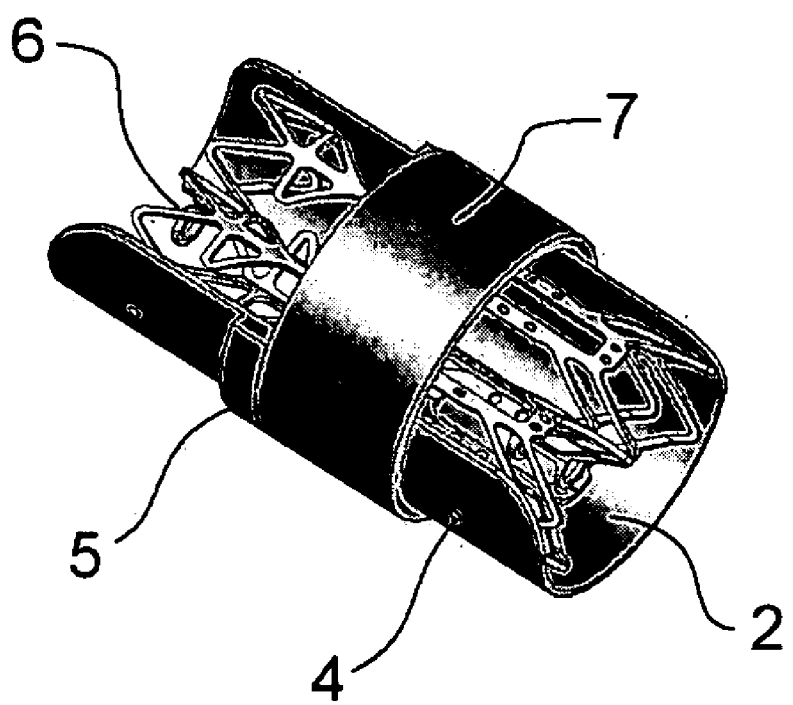
FIG. 9 shows a folded heart valve loosely disposed in the folding device. The folding device is loosely disposed within a retainer ring. Parts of the heart valve, including the tissue and cloth cuffs, have been removed for clarity.

FIGS. 7A and 7B show end and side views, respectively, of a folded heart valve 6 loosely disposed in the folding device 2. FIGS. 8 and 9 also show the folded valve 6 disposed within the folding device 2. The folding device 2 helps maintain the valve 6 in a folded configuration. FIG. 9 shows the folding device 2 loosely disposed within a retainer ring 7. The retainer ring 7 helps maintain the folding device 2 in a folded configuration and allows the folded valve 6 to be transferred to the target site.

By utilizing the systems and methods for folding a heart valve described herein, the size (i.e. largest diameter that can be measured) of the valve during the implantation process is reduced by approximately 1 to 50%.

After the valve 1 has been folded, the temporary suture 9 attached to the suture holes 4 may be removed. In one embodiment of the present invention, the folded valve 6 and folding device 2 may be transferred to a front loading valve receptacle 10. In another embodiment of the present invention, the folded valve 6 is transferred alone directly from the folding device 2 into a front loading valve receptacle 10. In another embodiment of the present invention, the folded valve 6 and folding device 2 may be transferred to a guide rail valve receptacle 15. In another embodiment of the present invention, the folded valve 6 and folding device 2 may be transferred to a top loading valve receptacle 17. In another embodiment of the present invention, the folded valve 6 and folding device 2 may be transferred to a retainer ring valve receptacle 18.

The folding device 2 and the folded valve 6 may be maintained in a folded position by inserting the folding device 2 into a retainer ring 7. The retainer ring 7 maintains the shape of the collapsed valve and folding device 2. In one embodiment of the present invention, the retainer ring 7 is adapted to connect to a handle 11. As such, the combined folding device 2, retainer ring 7, and handle 11 functions as a valve delivery system. In another embodiment of the present invention, the valve 1 is pushed into a retainer ring 7 adapted to connect to a handle 11. As such, the combined retainer ring 7 and handle 11 functions as a valve delivery system.

Delivery Systems: Front Loading Valve Receptacle

FIGS. 10 through 23 show different variations of the disclosed delivery systems.

Figure 10:
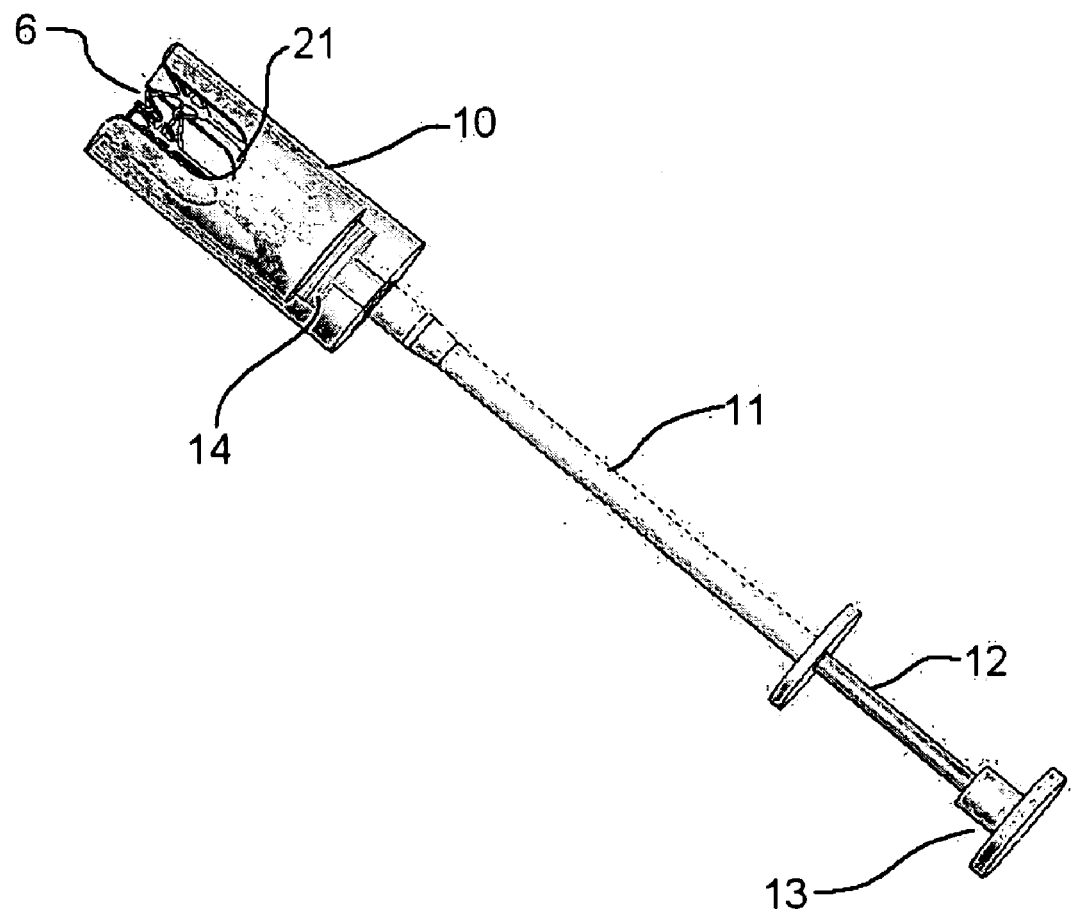
FIG. 10 shows a valve delivery system including a heart valve, front loading valve receptacle, handle, and plunger. Parts of the heart valve, including the tissue and cloth cuffs, have been removed for clarity.

FIG. 10 shows a delivery system that includes a front loading valve receptacle 10 adapted to receive a handle 11. The folded cardiac valve 6 is loosely disposed within the front loading valve receptacle 10. A plunger 12 is loosely disposed within the handle 11.

Figure 11:
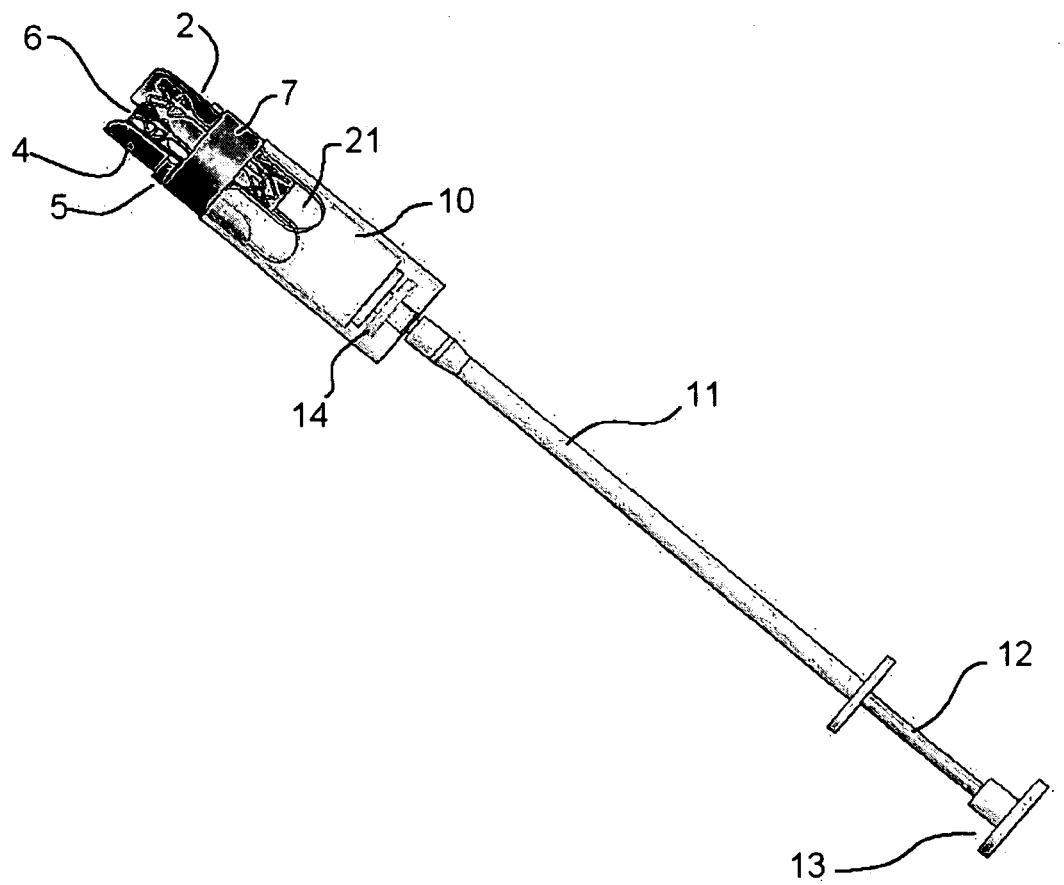
FIG. 11 shows a valve delivery system including a heart valve, front loading valve receptacle, handle, plunger, folding device, and retainer ring. Parts of the heart valve, including the tissue and cloth cuffs, have been removed for clarity.

FIG. 11 shows the same delivery system shown in FIG. 10. FIG. 11 also shows the folded valve 6 shown in FIG. 9 being transferred into the front loading valve receptacle 10. Here, the folded valve 6 is loosely disposed within the folding device 2. The folding device 2 is loosely disposed within the retainer ring 7. The stopper ring 5 limits the insertion of the folding device 2 into the front loading valve receptacle 10. Next, the folded valve 6 is inserted by sliding in the front loading valve receptacle 10. The stopper ring 5 and the folding device 2 is then removed, leaving the folded valve 6 loosely disposed within the front loading valve receptacle 10. The folded valve 6 may now be delivered to the annulus of the patient.

Figure 12A:
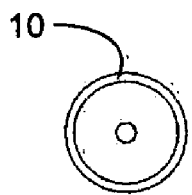
FIGS. 12A and 12B show end and side views, respectively, of a valve delivery system including a front loading valve receptacle and handle.
Figure 12B:
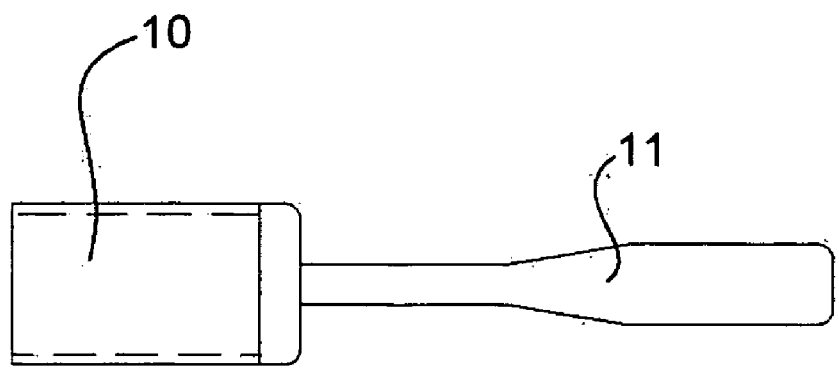
Figure 13A:
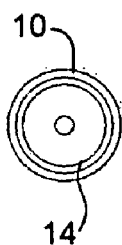
FIGS. 13A and 13B show end and side views, respectively, of a valve delivery system including a front loading valve receptacle, handle, and plunger.
Figure 13B:
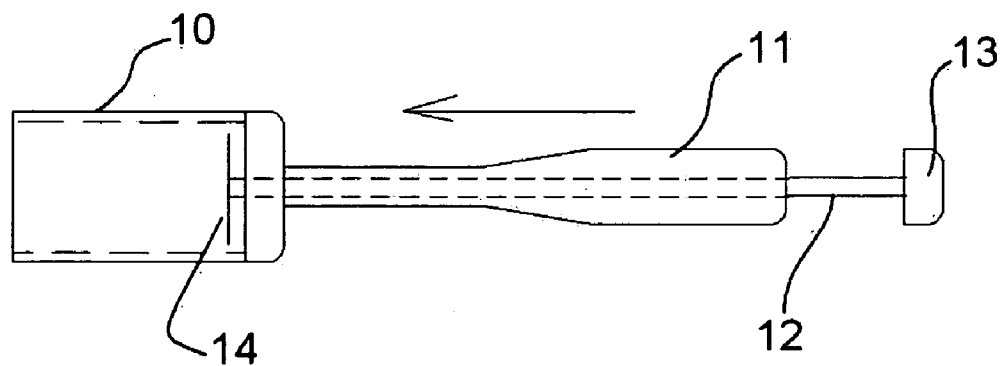

FIGS. 12A and 12B show end and side views, respectively, of a valve delivery system. The delivery system includes a front loading valve receptacle 10 adapted to receive a handle 11. FIGS. 13A and 13B show end and side views, respectively, of a valve delivery system including a front loading valve receptacle 10, handle 11, and plunger 12. The plunger 12 is loosely disposed within the handle 11. The plunger 12 may assist with the unfolding and delivery of the folded valve 6. Moving the plunger 12 in the direction of the folded valve 6 releases the folded valve 6 from the front loading valve receptacle 10.

Figure 14A:
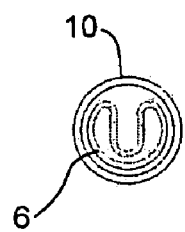
FIGS. 14A and 14B show end and side views, respectively, of a valve delivery system including a front loading valve receptacle, handle, plunger, and a folded valve.
Figure 14B:
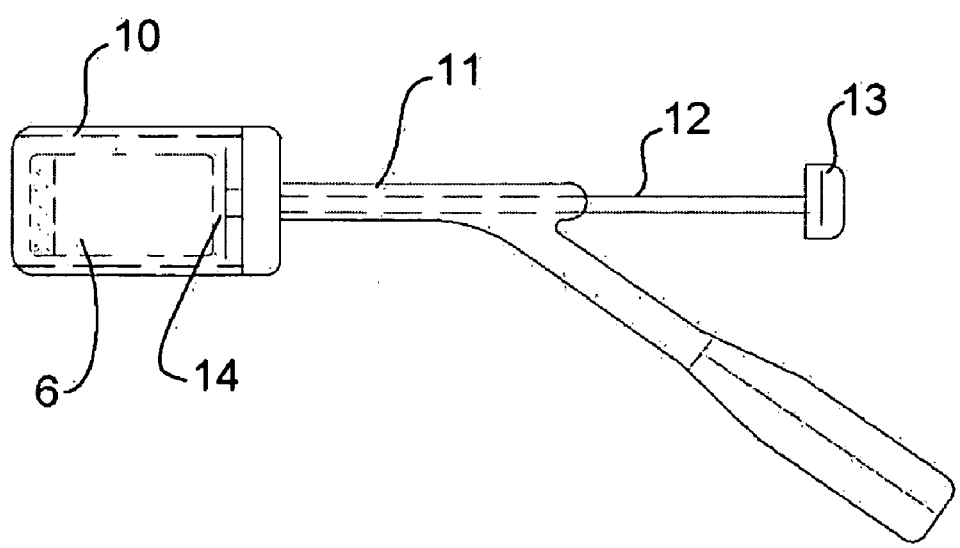
Figure 15A:
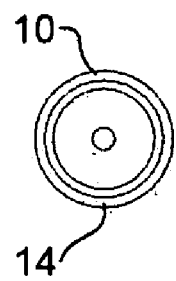
FIGS. 15A and 15B show end and side views, respectively, of a valve delivery system including a front loading valve receptacle, handle, and plunger.
Figure 15B:
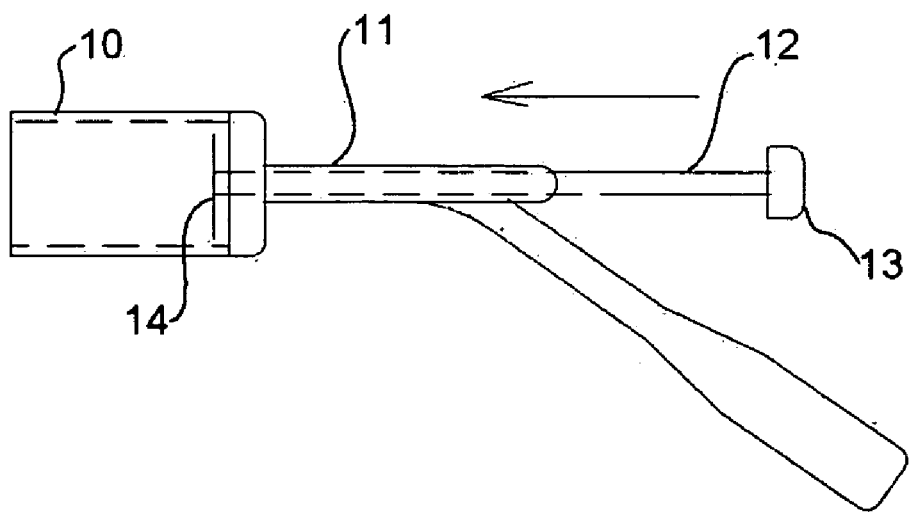

FIGS. 14A and 14B show end and side views, respectively, of a valve delivery system. The delivery system includes a front loading valve receptacle 10 adapted to receive a handle 11. A plunger 12 is loosely disposed within the handle 11. In FIG. 14B, the handle 11 is curved and not aligned with the plunger 12 over its entire length. This allows the user to grasp the handle 11 with the fingers of one hand and operate the plunger 12 with the thumb of the same hand. A folded valve 6 is shown loosely disposed within the front loading valve receptacle 10. FIGS. 15A and 15B show end and side views, respectively, of a valve delivery system including a front loading valve receptacle 10, handle 11, and plunger 12. Here, the plunger 12 has been moved in the direction of the arrow. The plunger 12, attached to the plunger plate 14, pushed the valve 1 out of the front loading valve receptacle 10, thereby releasing the valve.

In one embodiment of the present invention, the folded cardiac valve 6 is released by retracting the handle 11 while keeping the plunger 12 stationary. The plunger plate 14, which is attached to the distal portion of the plunger 12, prevents the folded valve 6 from moving while retracting the handle 11 and the front loading valve receptacle 10. A knob 13 attached to the proximal portion of the plunger 12 facilitates manipulation of the plunger 12. In another embodiment of the present invention, a plunger 12, plunger plate 14, and a plunger knob 13 are not utilized. In this embodiment, the valve 1 is released by pulling the entire delivery system away from the target site.

In one embodiment of the present invention, the front loading valve receptacle 10 includes one or more distal suture slots 21 that may be used to gain access to the folded valve 6 suture ring area, for example to insert sutures into the folded valve 6 for use during later implantation. In another embodiment of the current invention, the front loading valve receptacle 10 does not include any distal suture slots 21.

The valve receptacle 10 shown in FIG. 10 through FIG. 15 may be characterized as a front or distal valve receptacle since the folded valve 6 is inserted distal to the valve receptacle 10.

Delivery Systems: Guide Rail Valve Receptacle

Figure 16A:
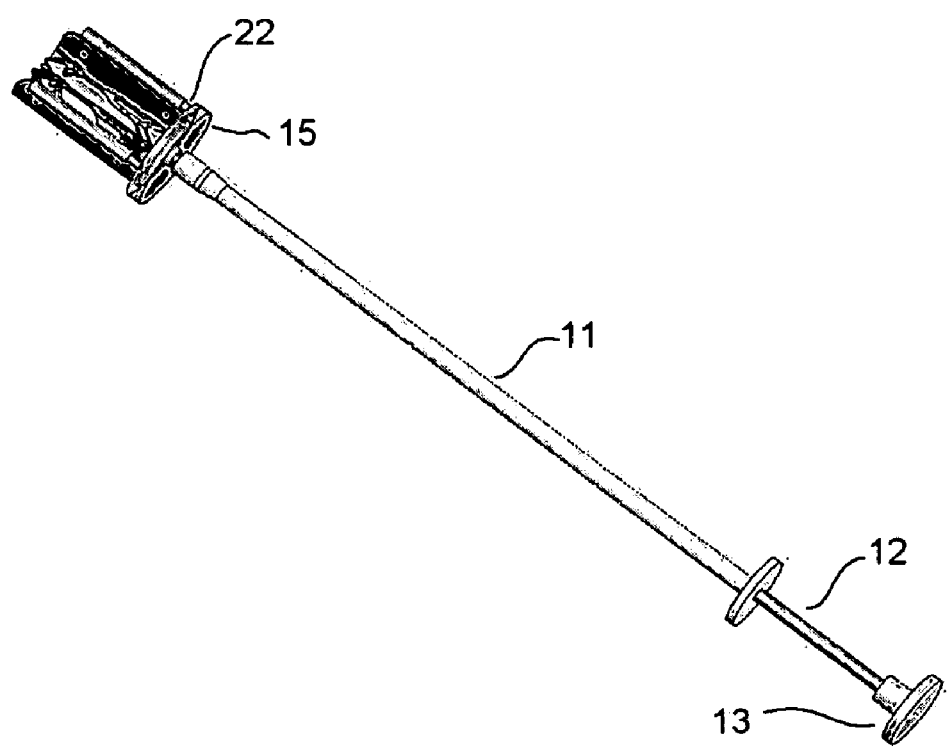
FIG. 16A shows a valve delivery system including a heart valve, folding device, handle, and plunger. Parts of the heart valve, including the tissue and cloth cuffs, have been removed for clarity.
Figure 16B:
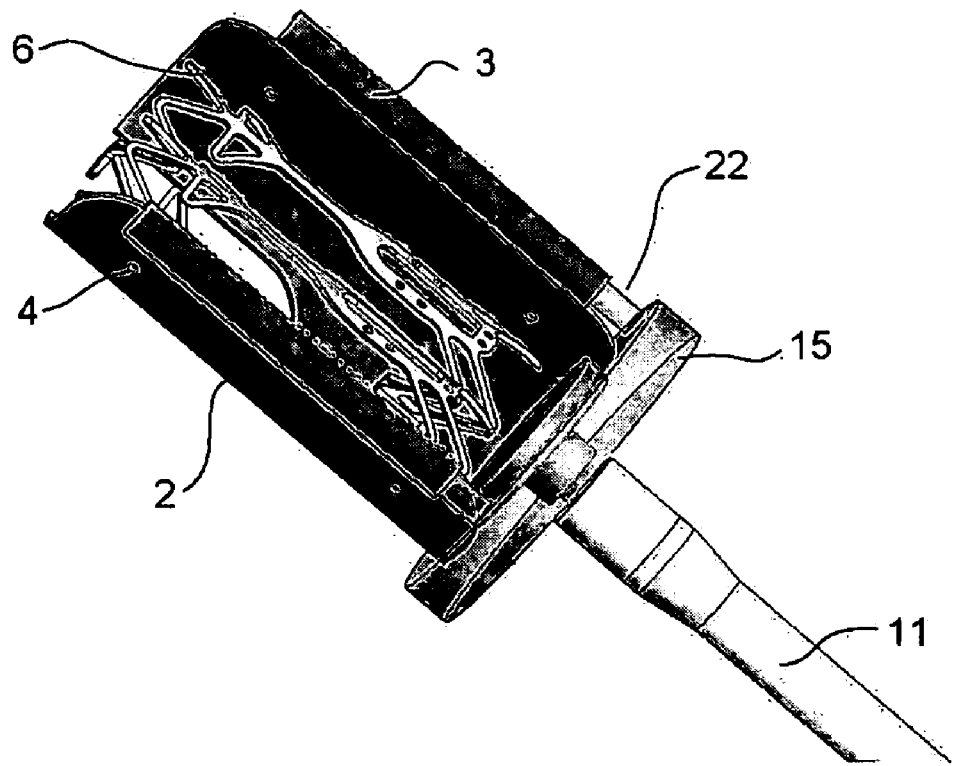
FIG. 16B shows a close-up view of the valve delivery system of FIG. 16A. Parts of the heart valve, including the tissue and cloth cuffs, have been removed for clarity.

FIGS. 16A and 16B show a delivery system with a different valve receptacle. FIGS. 16A and 16B show the folded valve 6 disposed within the folding device 2. The two locking bars 3 are loosely disposed around the two guide rails 22 that form the guide rail valve receptacle 15. Once the valve 1 has been folded, the folded valve 6 and the folding device 2 may be attached to the guide rail valve receptacle 15 by sliding the folding device 2 and the folded valve 6 between the two guide rails 22 part of the guide rail valve receptacle 15.

In one embodiment of the present invention, the cardiac valve 1 is released by retracting the handle 11 while keeping the plunger 12 stationary. A plunger plate 14 is attached to the distal portion of the plunger 12. The plunger plate 14 prevents the valve from moving while retracting the handle 11. A knob 13 is attached to the proximal portion of the plunger 12. In another embodiment of the present invention, a plunger 12, plunger plate 14, and a plunger knob 13 are not utilized. Rather, the valve 1 is released by pulling the delivery system away from the target site. In order for such a method of releasing the folded valve 6 to work properly, the folded valve 6 must exert a retaining force against the annulus as it unfolds, thereby preventing the folded valve 6 from moving with respect to the annulus. Alternatively, the user can employ a suture or similar means to retain the folded valve 6 at the target site.

In one embodiment of the present invention, the guide rail valve receptacle 15 includes one or more suture slots 21 that may be used gain access to the folded valve 6, such as to insert sutures into the valve for use during implantation. In another embodiment of the current invention, the guide rail valve receptacle 15 does not include any suture slots 21.

Delivery Systems: Folding Device Valve Receptacle

Figure 17:
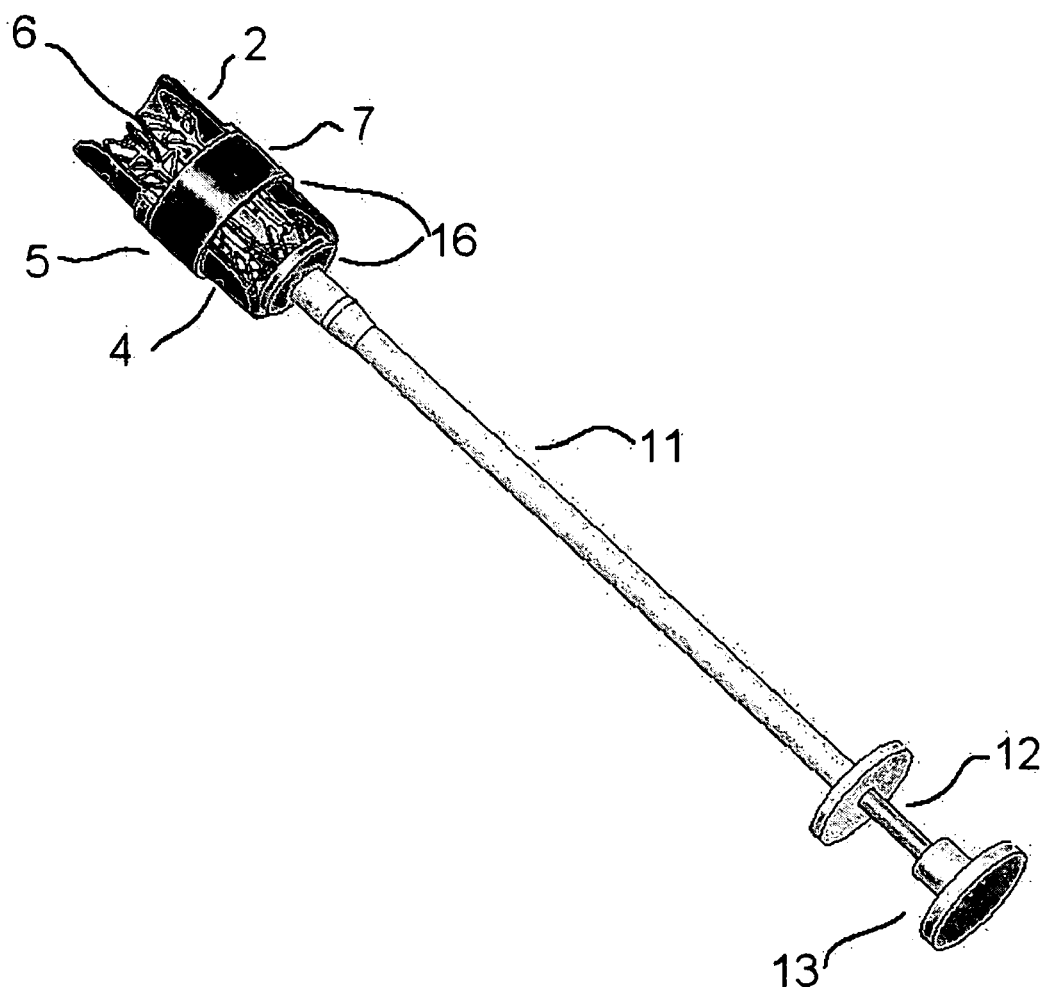
FIG. 17 shows a valve delivery system including a heart valve, folding device, handle, retainer ring, and plunger. Parts of the heart valve, including the tissue and cloth cuffs, have been removed for clarity.

FIG. 17 shows the folded valve 6 loosely disposed within the folding device 2. The folding device 2 is in turn loosely disposed within the retainer ring 7. The combined folding device 2 and retainer ring 7 shown in FIG. 9 is here dubbed a folding device valve receptacle 16. The folding device valve receptacle 16 is adapted to receive a handle 11.

In one embodiment of the present invention, the cardiac valve 1 is released by retracting the handle 11 while keeping the plunger 12 stationary. A plunger plate 14 is attached to the distal portion of the plunger 12. The plunger plate 14 prevents the valve from moving while retracting the handle 11. A knob 13 is attached to the proximal portion of the plunger 12. In another embodiment of the present invention, a plunger 13, plunger plate 14, and a plunger knob 13 is not utilized. As such, the valve 1 is released by pulling the delivery system away from the target site. In one embodiment of the present invention, the handle is curved to allow better view of or easier access to the target implantation site.

In one embodiment of the present invention, the folding device valve receptacle 16 includes one or more suture slots 21 that may be used to gain access to the suture ring of the folded valve 6, such as to insert sutures into the valve suture ring for use during implantation. In another embodiment of the current invention, the folding device valve receptacle 16 does not include any suture slots 21.

Delivery Systems: Top Loading Valve Receptacle

Figure 18:
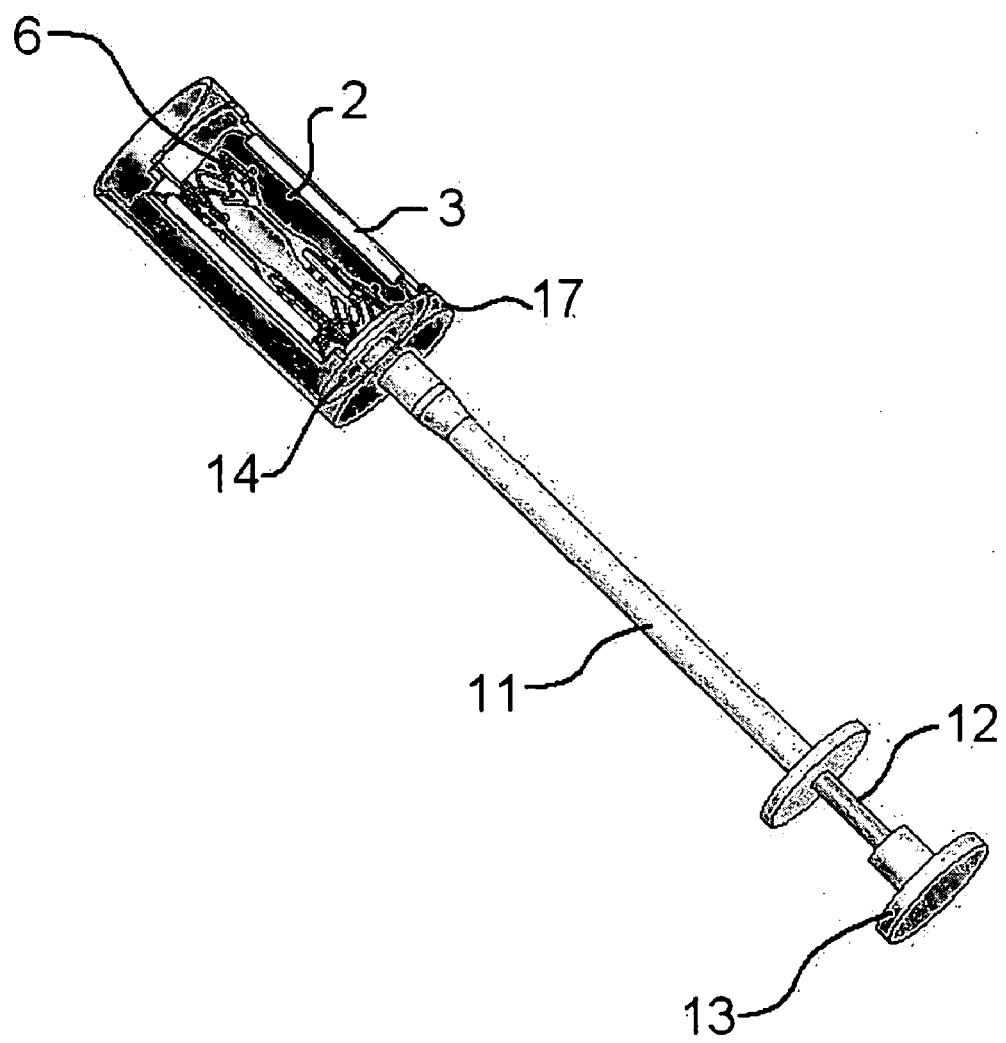
FIG. 18 shows a valve delivery system including a top loading valve receptacle, heart valve, folding device, handle, and plunger. Parts of the heart valve, including the tissue and cloth cuffs, have been removed for clarity.

FIG. 18 shows a delivery system with a different valve receptacle. FIG. 18 shows the folded valve 6 loosely disposed within the folding device 2, also shown in FIG. 8. Once the valve 6 is folded within the folding device 2, the folding device 2 may be inserted into the top loading window of the top loading valve receptacle 17. FIG. 18 shows the folding device 2 loosely disposed within the top loading valve receptacle 17. The top loading valve receptacle 17 is adapted to receive a handle 11.

Figure 19A:
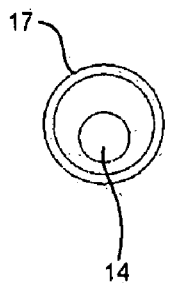
FIGS. 19A and 19B show end and side views, respectively, of a valve delivery system including a top loading valve receptacle, handle, and plunger.
Figure 19B:
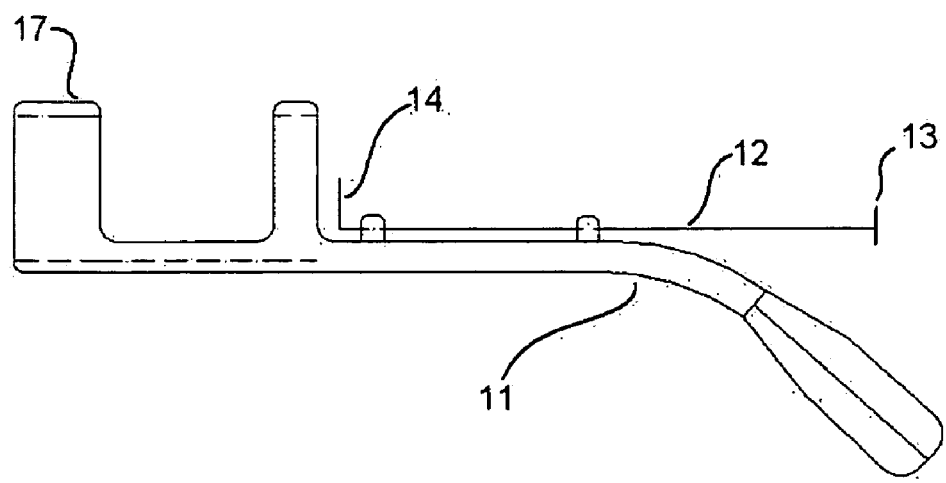

FIGS. 19A and 19B show end and side views, respectively, of a valve delivery system that includes a top loading valve receptacle 17, handle 11, plunger 12, a plunger plate 14, and a curved handle 11.

Figure 20A:
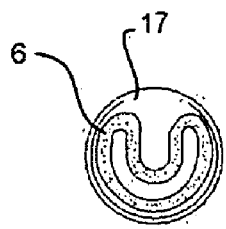
FIGS. 20A and 20B show end and side views, respectively, of a valve delivery system including a top loading valve receptacle, folded valve, folding device, handle, and plunger.
Figure 20B:
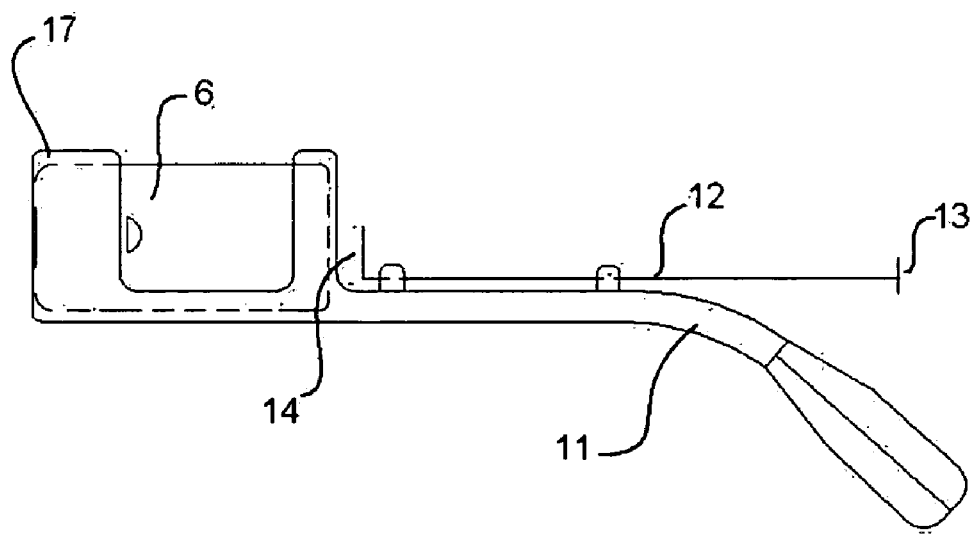

FIGS. 20A and 20B show the same delivery system seen in FIGS. 19A and 19B, respectively. In FIG. 20A, the folding device 2 and valve 6 is also shown inserted into the top loading valve receptacle 17.

In one embodiment of the present invention, the cardiac valve 1 is released by retracting the handle 11 while keeping the plunger 12 stationary. A plunger plate 14 is attached to the distal portion of the plunger 12. The plunger plate 14 prevents the valve from moving while retracting the handle 11. A knob 13 is attached to the proximal portion of the plunger 12. In another embodiment of the present invention, a plunger 13, plunger plate 14, and a plunger knob 13 are not utilized. Here, the valve 1 is released by pulling the delivery system away from the target site. In one embodiment of the present invention, the handle is curved to allow better view or easier access to the target implantation site.

In one embodiment of the present invention, the top loading valve receptacle 17 includes one or more suture slots 21 that may be used gain access to the folded valve, such as to insert sutures into the valve for use during implantation. In another embodiment of the current invention, the top loading valve receptacle 17 does not include any suture slots 21.

Delivery Systems: Retainer Ring Valve Receptacle

A valve delivery system is provided that includes a retainer ring 7 adapted to receive a handle 11. When the retainer ring 7 is adapted to receive a handle 11 and used to transfer and deliver a valve, the retainer ring 7 is dubbed a retainer ring valve receptacle 18. In one embodiment, the folded cardiac valve 6 is loosely disposed within the retainer ring valve receptacle 18. In another embodiment, the folded cardiac valve 6 is loosely disposed within a folding device 2, which in turn is disposed within the retainer ring valve receptacle 18. The folded cardiac valve 6 is released by pulling the delivery system away from the target site, thereby leaving the unfolded cardiac valve 1 disposed in the annulus. In another embodiment, a plunger 12 and plunger plate 14 may be used to release the folded valve 6.

Figure 21:
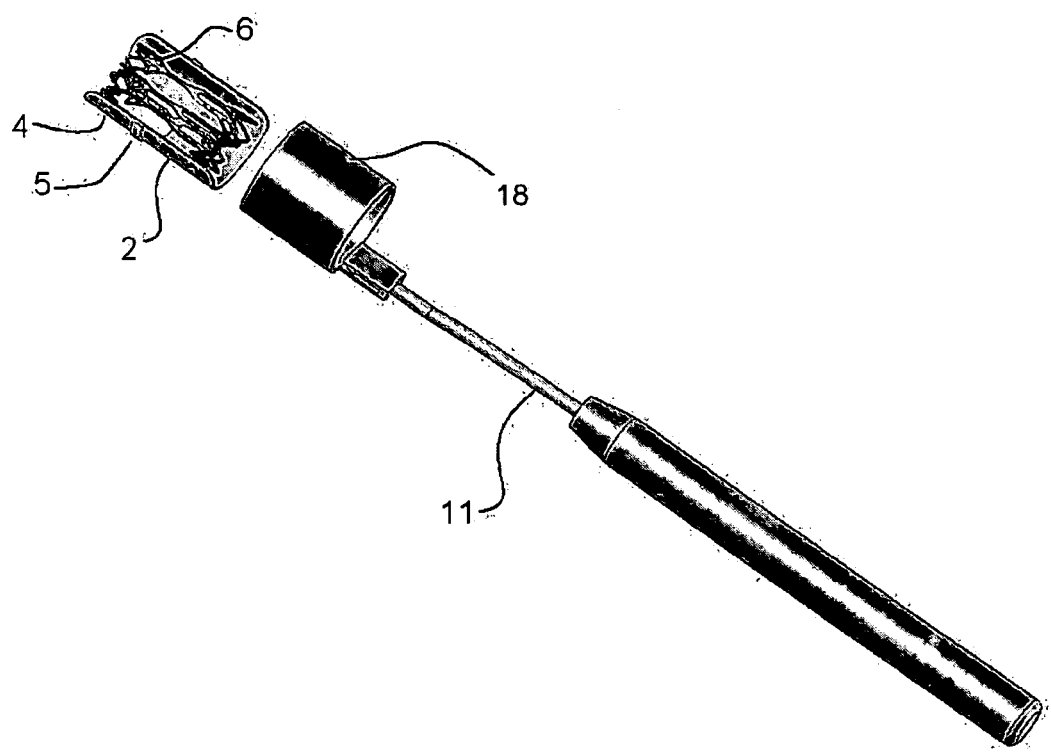
FIG. 21 shows a valve delivery system including a folding device, heart valve, retainer ring, handle, and plunger in which the folded valve and the folding device is in the process of being transferred to the retainer ring valve receptacle.
Figure 22:
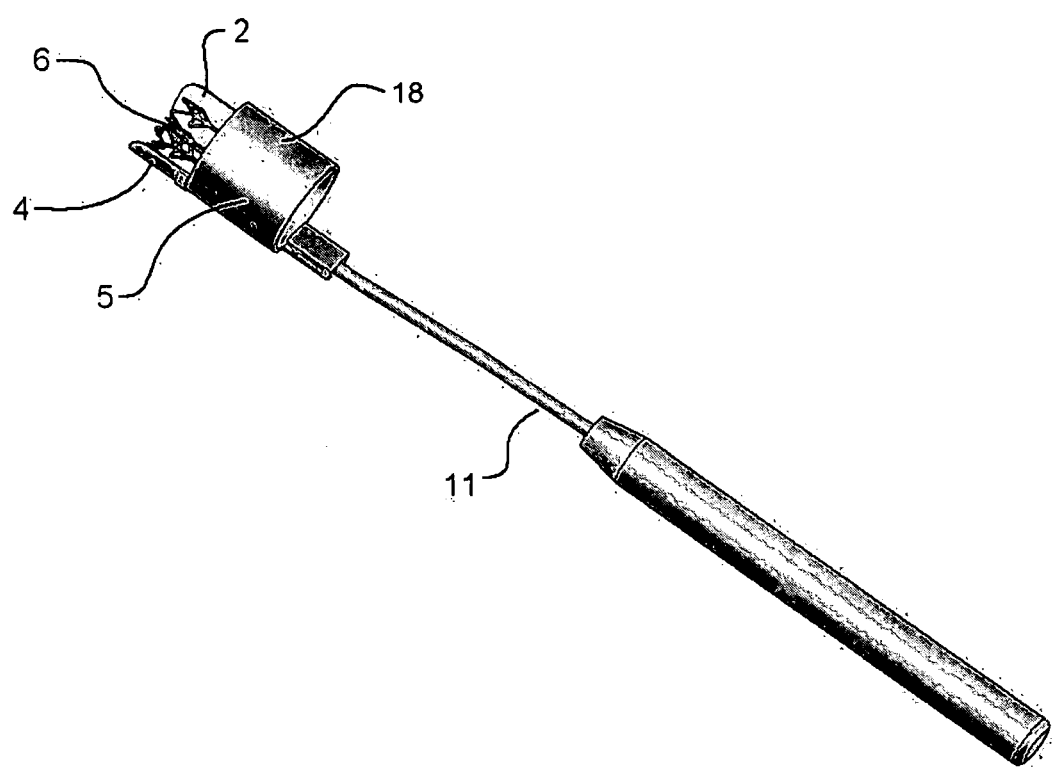
FIG. 22 shows a perspective view of the valve delivery system of FIG. 21 wherein the folded valve and the folding device are inserted into the retainer ring.
Figure 23:
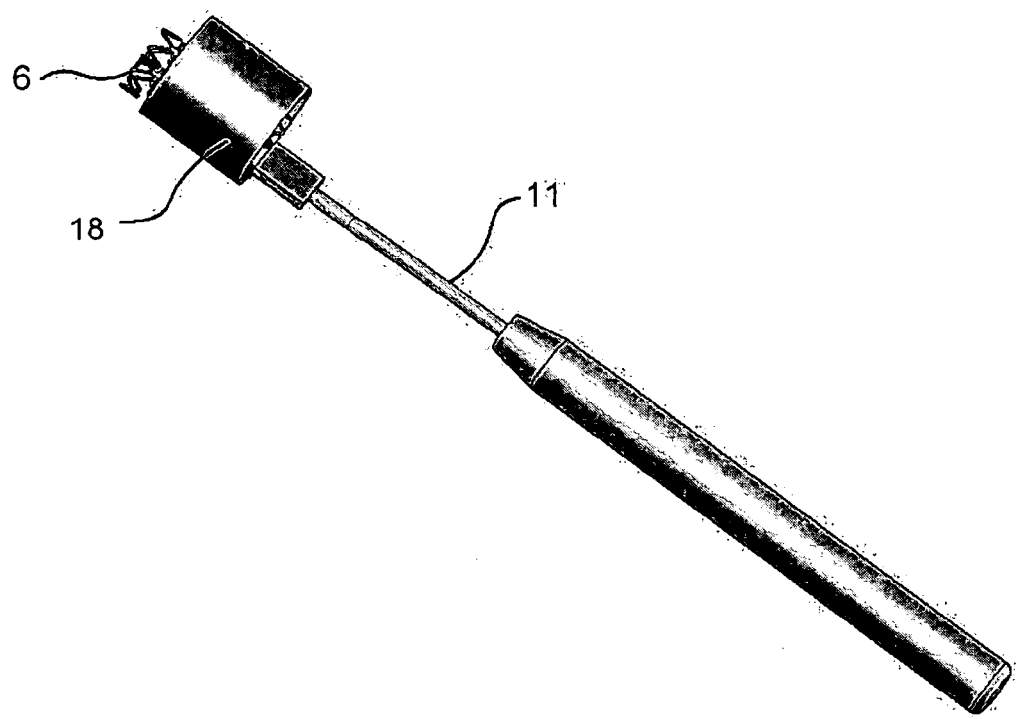
FIG. 23 shows a perspective view of the valve delivery system of FIG. 21 wherein the folded valve is inserted into the retainer ring.

FIG. 21 shows such a delivery system. A retainer ring valve receptacle 18 is adapted to receive a handle 11. The folded prosthetic valve 6 is shown folded within the folding device 2. In one embodiment, the folded prosthetic valve 6 is moved directly into the retainer ring valve receptacle 18 as shown in FIG. 23. In another embodiment, the folding device 2 and folded prosthetic valve 6 may jointly be inserted into the retainer ring valve receptacle 18 as shown in FIG. 22. In yet another embodiment, the folding device 2 is removed from the delivery system shown in FIG. 22, leaving the folded valve 6 loosely disposed within the retainer ring valve receptacle 18 as shown in FIG. 23.

General Considerations

The folding device 2, handle 11, front loading valve receptacle 10, guide rail valve receptacle 15, folding device valve receptacle 16, top loading valve receptacle 17, retainer ring valve receptacle 18, plunger 12, plunger plate 14, and retainer ring 7 may be made of metal, plastic, or polymeric plastic materials that can be cleaned or sterilized in an autoclave. The delivery system may be disposable or reusable. Components of the delivery system or folding device may also be made out of a transparent material thereby making folding and valve delivery easier.

In one embodiment of the present invention, the handle 11 is curved to allow better view of or easier access to the target implantation site. In one embodiment, the handle 11 is straight. In another embodiment, the handle 11 is centered in relation to axis of the folded valve 6. In another embodiment, the handle is offset to the side in relation to the axis of the folded valve 6.

In one embodiment of the current invention, a front loading valve receptacle 10, can be adapted and used to size the valve annulus or orifice before using the delivery system to deliver the folded valve 6. The external diameter of the front loading valve receptacle 10 may be used to size the valve annulus or orifice. Front loading valve receptacles 10 of different diameters may be inserted into the valve annulus until a diameter matching the valve annulus is found. Annulus size is determined by the diameter of the front loading valve receptacle 10, which may be engraved onto the valve receptacle 10. Once the proper valve size is selected, the valve 1 may be folded using the folding device and inserted into the front loading valve receptacle 10. In another embodiment of the present invention, a folding device valve receptacle 16 can be adapted and used to size the valve annulus or orifice before using the delivery system to deliver the folded valve 6. In another embodiment of the present invention, a top loading valve receptacle 17 can be adapted and used to size the valve annulus or orifice before using the delivery system to deliver the folded valve 6. In another embodiment of the present invention, a retainer ring 7 can be adapted and used to size the valve annulus or orifice before delivering the folded valve 6. In another embodiment of the present invention, a retainer ring valve receptacle 18 can be adapted and used to size the valve annulus or orifice before using the delivery system to deliver the folded valve 6.

Front loading valve receptacle 10, guide rail valve receptacle 15, folding device valve receptacle 16, top loading valve receptacle 17, and retainer ring valve receptacle 18, described herein may be manufactured in different sizes to accept valves from 1 mm to 70 mm. In one embodiment, the valve receptacles described herein, are interchangeable. That is, a particular handle may accept different valve receptacle sizes.

Alternative Delivery Device

Figure 24:
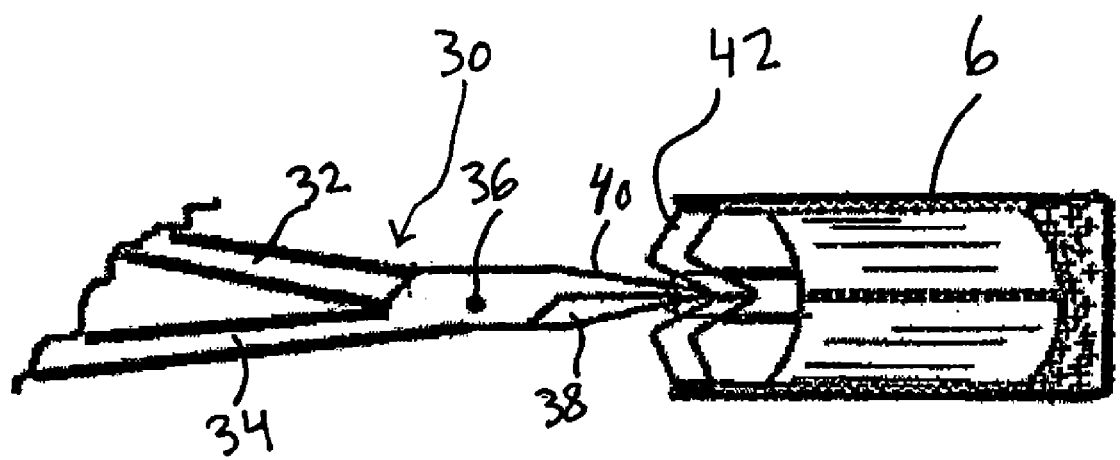
FIG. 24 is a side view of a folded valve.

As discussed in detail above, FIGS. 10-23 illustrate numerous exemplary embodiments of delivery systems that may be used after the valve is folded to hold, transfer, and deliver a cardiac valve during a valve implantation process into a valve annulus. However, as will be appreciated by those skilled in the art, numerous other systems and devices may be used in order to hold and deliver a cardiac valve that was folded using the method and system and the folding device disclosed. FIG. 24 illustrates one such alternative device.

Particularly, FIG. 24 is a side view of the folded valve 6 after removal from a folding device, such as folding device 2. Although the folded valve 6 may be folded using a process similar to that previously described in reference to FIGS. 6A-6B and 7A-7B, those skilled in the art will appreciate that any suitable folding process and device within the scope of the present invention may be used. As illustrated in FIG. 24, rather than inserting the folded valve 6 into a front loading valve receptacle 10, a guide rail valve receptacle 15, a folding device valve receptacle 16, a top loading valve receptacle 17, or a retainer ring valve receptacle 18, the folded valve 6 may instead be grasped from the rear side with a surgical clamp 30. In one exemplary embodiment, the surgical clamp 30 includes a first handle portion 32 and a second handle portion 34 connected with any suitable connection member 36, such as a hinge. As further illustrated in FIG. 24, the first and second handle portions 32 and 34 include first and second grasping members 38 and 40, respectively. As will be appreciated by those skilled in the art, rotating the first handle portion 32 with respect to the second handle portion 34 about the connection member 36 causes corresponding movement between the first and second grasping members 38 and 40.

During operation, once the folding device 2 has been utilized to create the folded valve 6 as shown in FIG. 7A, the surgical clamp 30 may be manipulated in order to grasp a portion of the outflow end 42 of the folded valve 6 between the first and second grasping members 38 and 40. Once the folded valve 6 has been securely grasped between the first and second grasping members 38 and 40, the folding device 2 may be removed (as illustrated in FIG. 24), such as by removing temporary suture 9 attached to suture holes in the folding device 2. Once the folding device 2 has been removed, the folded valve 6 is maintained in the folded and collapsed position by the surgical clamp 30. The surgical clamp 30 may then be used to directly transfer and deliver the folded valve 6 to a target site in or near the heart. As those skilled in the art will appreciate, subsequently manipulating the first and second handle portions 32 and 34 to cause separation between the first and second grasping members 38 and 40 will release the folded valve 6 into the target site, thereby allowing the valve to expand to a normal unfolded configuration within the patient annulus of implant.

One benefit of the surgical clamp in accordance with the present invention is that it provides for a substantially unobstructed view during valve implantation. For example, in one exemplary procedure using the surgical clamp 30, while maintaining the valve in its collapsed and folded position, the surgeon may then guide the valve along the aortic root to the site of the patient valve annulus. Throughout the implantation process, the surgeon may ensure the accurate placement of the valve into the annulus of implant. Another benefit of the surgical clamp in accordance with the present invention is that is provides for a simplified and efficient valve implantation process.

Obviously, numerous variations and modifications can be made within departing from the spirit of the present invention. Therefore, it should be clearly understood that the forms of the present invention described above and shown in the figures of the accompanying drawings are illustrative only and are not intended to limit the scope of the present invention.

What is claimed is:

1. A valve folding assembly comprising:
   a valve holder comprising an open-faced, semi-cylindrical flexible tube having a curvature and length substantially matching that of a prosthetic valve;
   a plurality of elongate locking bars operably connected to said semi-cylindrical flexible tube along a longitudinal axis thereof;
   one or more suture slots located on the valve holder;
   a stopper ring structured to at least partially circumferentially surround said semi-cylindrical tube; and
   a valve receptacle configured to receive the valve holder, said valve receptacle including at least two guide rails attached to a disk, said guide rails adapted to engage the locking bars of the valve holder.

2. The valve folding assembly of claim 1, further comprising sutures tied between suture holes located on opposite sides of the valve holder; and a prosthetic valve retained within the valve holder.

3. The valve folding assembly of claim 1 further comprising a handle operably attached to said valve receptacle.

4. The valve folding assembly of claim 3, further comprising a plunger loosely disposed within the handle.

* * * * *